US00PP33758P2

(12) United States Plant Patent
Vitten et al.

(10) Patent No.: US PP33,758 P2
(45) Date of Patent: Dec. 21, 2021

(54) RASPBERRY PLANT VARIETY NAMED 'DRISRASPTWENTYONE'

(50) Latin Name: ***Rubus idaeus* L.**
Varietal Denomination: DrisRaspTwentyOne

(71) Applicant: Driscoll's, Inc., Watsonville, CA (US)

(72) Inventors: Matthias D. Vitten, Watsonville, CA (US); Kyle Rak, Watsonville, CA (US); Luis Miguel Rodriguez, Watsonville, CA (US); James Heilig, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 17/016,222

(22) Filed: Sep. 9, 2020

(51) Int. Cl.
*A01H 5/08* (2018.01)
*A01H 6/74* (2018.01)

(52) U.S. Cl.
USPC ..... Plt./204

(58) Field of Classification Search
USPC ..... Plt./204
CPC ... A01H 5/08; A01H 5/02; A01H 6/74; A01H 6/749; A01H 6/7499; A01H 5/00
See application file for complete search history.

(56) References Cited

U.S. PATENT DOCUMENTS

PP4,486 P 11/1979 Reiter
PP6,493 P 12/1988 Wilhelm
PP7,436 P 2/1991 Ackerman
PP7,437 P 2/1991 Ackerman
PP7,528 P 5/1991 Ackerman
PP8,022 P 11/1992 Wilhelm
PP8,027 P 11/1992 Wilhelm
PP9,340 P 10/1995 Wilhelm et al.
PP9,653 P 10/1996 Wilhelm et al.
PP9,696 P 11/1996 Fear
PP11,067 P 9/1999 Fear et al.
PP11,087 P 10/1999 Fear et al.
PP11,094 P 10/1999 Fear et al.
PP11,102 P 10/1999 Fear et al.
PP14,761 P2 5/2004 Fear et al.
PP14,781 P2 5/2004 Fear et al.
PP14,804 P2 * 5/2004 Fear ..... A01H 6/7499 Plt./204
PP14,860 P2 6/2004 Fear et al.
PP14,903 P2 6/2004 Fear et al.
PP14,904 P2 6/2004 Fear et al.
PP18,658 P3 3/2008 Fear et al.
PP18,659 P3 3/2008 Fear et al.
PP19,137 P3 8/2008 Harrison et al.
PP19,656 P2 1/2009 Hamilton et al.
PP22,246 P3 11/2011 Hamilton et al.
PP22,731 P2 5/2012 Fear et al.
PP23,477 P3 3/2013 Hamilton et al.
PP24,610 P3 7/2014 Hamilton et al.
PP25,044 P3 11/2014 Hamilton et al.
PP25,045 P3 11/2014 Hamilton et al.
PP27,644 P3 2/2017 Hamilton et al.
PP28,775 P2 12/2017 Hamilton et al.
PP28,856 P3 1/2018 Vitten et al.
PP29,402 P2 6/2018 Vitten et al.
PP30,577 P2 * 6/2019 Vitten ..... A01H 6/7499 Plt./204
PP30,733 P2 7/2019 Hamilton et al.
PP31,850 P2 6/2020 Hamilton et al.

OTHER PUBLICATIONS

Cousineau et al., "Use of Isoenzyme Analysis to Characterize Raspberry Cultivars and Detect Cultivar Mislabeling", HortScience vol. 27, No. 9, Sep. 1992, pp. 1023-1025.
Vitten et al., Unpublished U.S. Appl. No. 17/016,227, filed Sep. 9, 2020, titled "Raspberry Plant Variety Named 'DrisRaspTwentyTwo'".
Vitten et al., Unpublished U.S. Appl. No. 17/016,220, filed Sep. 9, 2020, titled "Raspberry Plant Variety Named 'DrisRaspTwenty'".
Harrison et al., Unpublished U.S. Appl. No. 17/003,824, filed Aug. 26, 2020, titled "Raspberry Plant Variety Named 'DrisRaspNineteen'".
Vitten et al., Unpublished U.S. Appl. No. 17/003,817, filed Aug. 26, 2020, titled "Raspberry Plant Variety Named 'DrisRaspEighteen'".
Vitten et al., Unpublished U.S. Appl. No. 16/602,687, filed Nov. 19, 2019, titled "Raspberry Plant Variety Named 'DrisRaspSeventeen'".
Vitten et al., Unpublished U.S. Appl. No. 16/501,853, filed Jun. 19, 2019, titled "Raspberry Plant Named 'DrisRaspFifteen'".
Williams et al., "DNA Polymorphisms Amplified by Arbitrary Primers are useful as Genetic Markers", Nucleic Acids Research, vol. 18, No. 22, 1990, pp. 6531-6535.

* cited by examiner

*Primary Examiner* — June Hwu
(74) *Attorney, Agent, or Firm* — Morrison & Foerster LLP

(57) ABSTRACT

A new and distinct variety of raspberry plant named 'DrisRaspTwentyOne', particularly selected for its fruit size and flavor, is disclosed.

4 Drawing Sheets

RASPBERRY PLANT VARIETY NAMED 'DRISRASPTWENTYONE'

Latin name:

Botanical classification: *Rubus idaeus* L.

Varietal denomination: The varietal denomination of the claimed variety of raspberry plant is 'DrisRaspTwentyOne'.

BACKGROUND OF THE INVENTION

Raspberries are the edible fruit of a multitude of plant species in the genus *Rubus* of the rose family. Most raspberry species are in the subgenus *Idaeobatus*. Raspberry plants are perennial plants with woody stems. Many of the most important modern commercial red raspberry cultivars derive from hybrids between *R. idaeus* and *R. strigosus*. Recent breeding has resulted in cultivars that are thornless and more strongly upright, not needing staking.

Both the red and the black raspberry species have albino-like pale-yellow natural or horticultural variants. Fruits from such plants are called golden raspberries or yellow raspberries. Most pale-fruited raspberries commercially sold in the eastern United States are derivatives of red raspberries. Yellow-fruited variants of the black raspberry are sometimes grown in home gardens. Despite their dissimilar appearance, golden raspberries retain the distinctive flavor of their respective red or black species.

An individual raspberry fruit is made up of around 100 drupelets, each of which contains a juicy pulp and a single central seed. A raspberry bush can yield several hundred berries a year. Unlike blackberries and dewberries, a raspberry has a hollow core once it is removed from the receptacle.

Raspberries are traditionally planted in the winter as dormant canes, but planting plugs produced by tissue culture is also common. Additionally, the long cane production method consists of growing canes for one year in cold climates where the bud break is early, and then transplanting the canes to warm climates where they quickly flower and can produce an early season crop. A very vigorous crop, raspberries spread well and can be considered invasive, using extended underground shoots (also known as suckers or basal shoots) that can develop roots and individual plants.

Raspberries are a popular fruit that are recognized for their antioxidants, high fiber, and as a good source of vitamin C. Raspberry fruit is typically consumed as fresh fruit, individually quick frozen (IQF) fruit, or in prepared foods, such as purées, juices, jellies, jams, grocery items, baked goods, and snack foods.

Raspberry is an important and valuable commercial fruit crop, widely grown in all temperate regions of the world. Accordingly, there is a need for new varieties of raspberry plant. In particular, there is a need for improved varieties of raspberry plant that are stable, high yielding, and agronomically sound.

SUMMARY OF THE INVENTION

In order to meet these needs, the present invention is directed to an improved variety of raspberry plant. In particular, the invention relates to a new and distinct variety of raspberry plant (*Rubus idaeus* L.), which has been denominated as 'DrisRaspTwentyOne'.

Raspberry plant variety 'DrisRaspTwentyOne' was discovered in Santa Cruz County, Calif. in October of 2016 and originated from a cross between the female parent 'DrisRaspTwelve' (U.S. Plant Pat. No. 30,577) and the proprietary male parent 'RC448.4' (unpatented). The original seedling of the new variety was first asexually propagated in Santa Cruz County, Calif. via root cuttings in October 2016.

'DrisRaspTwentyOne' was subsequently asexually propagated via root cuttings, and has undergone testing in Santa Cruz County, Calif. for four years (2016 to 2020). The present variety has been found to be stable and reproduce true to type through successive asexual propagations via root cuttings and tissue culture.

'DrisRaspIwentyOne' was particularly selected for its fruit size and flavor.

BRIEF DESCRIPTION OF THE DRAWINGS

This new raspberry plant is illustrated by the accompanying photographs. The colors shown are as true as can be reasonably obtained by conventional photographic procedures. The photographs are of plants that are one year old.

DETAILED BOTANICAL DESCRIPTION

Figure 1:
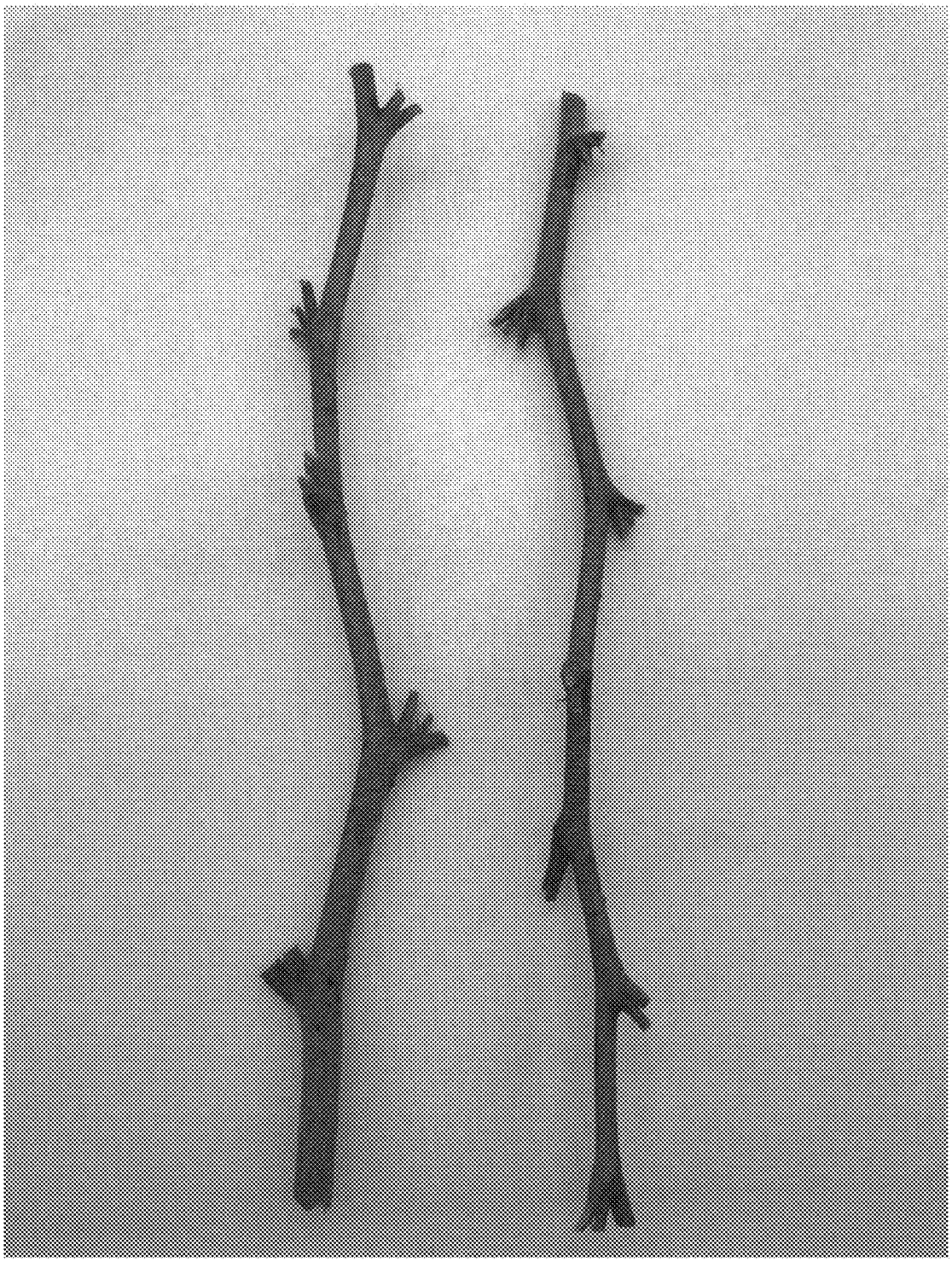
FIG. 1 illustrates sections of primocanes of raspberry variety 'DrisRaspTwentyOne'.
Figure 2:
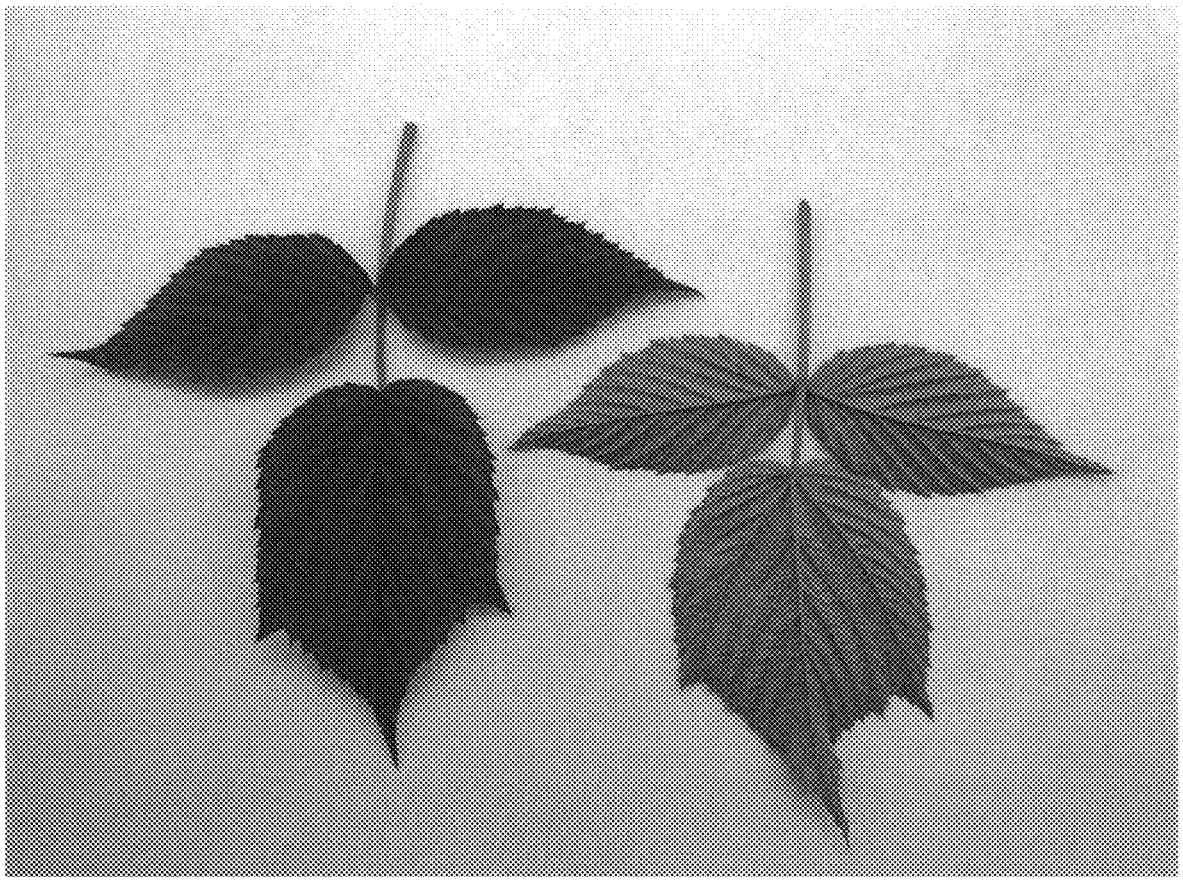
FIG. 2 illustrates the upper surface (left leaf) and the lower surface (right leaf) of leaves of raspberry variety 'DrisRaspTwentyOne'.
Figure 3:
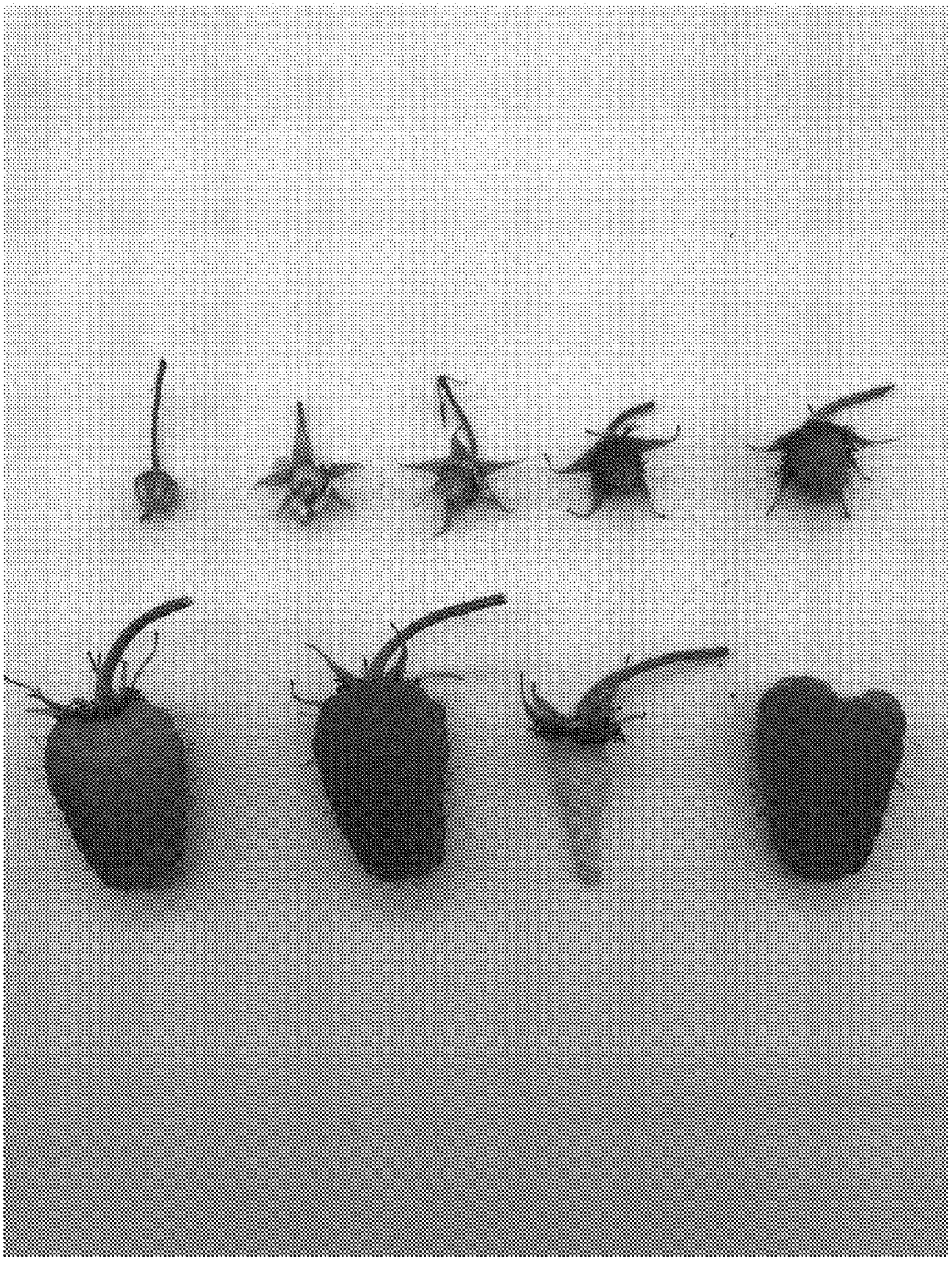
FIG. 3 illustrates flowers and fruit of raspberry variety 'DrisRaspTwentyOne' at various stages of development.
Figure 4:
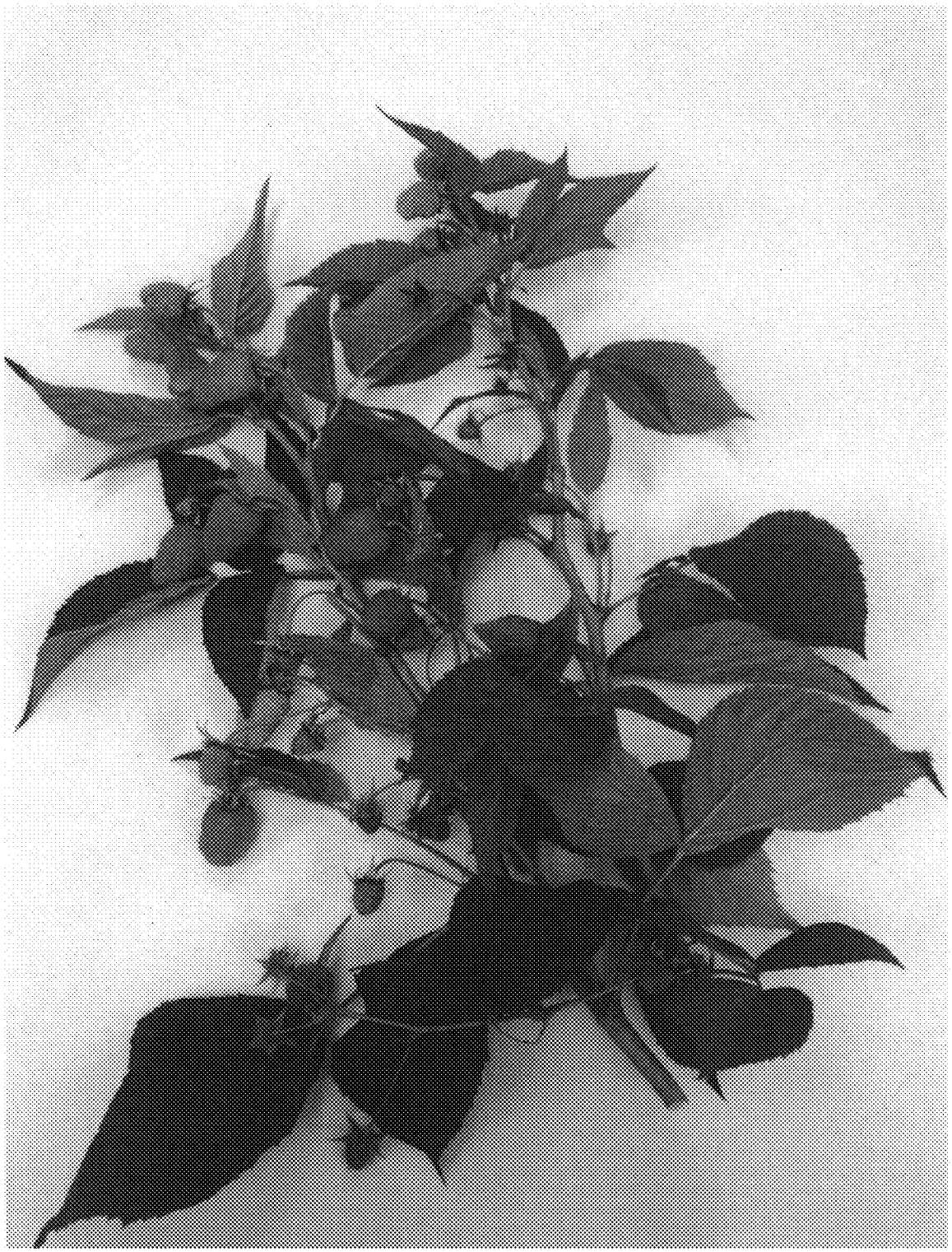
FIG. 4 illustrates a section of a plant with primocanes of raspberry variety 'DrisRaspTwentyOne'.

The following descriptions set forth the distinctive characteristics of 'DrisRaspTwentyOne'. Unless where otherwise noted, the data that define these characteristics are based on observations taken from 'DrisRaspTwentyOne' plants that were one year old, grown in Santa Cruz County, Calif. from 2016 to 2020. These descriptions are in accordance with UPOV terminology. Color designations, color descriptions, and other phenotypical descriptions may deviate from the stated values and descriptions depending upon variation in environmental, seasonal, climatic and cultural conditions. 'DrisRaspTwentyOne' has not been observed under all possible environmental conditions. The indicated values represent averages calculated from measurements of several plants. Color references are primarily to The R.H.S. Colour Chart of The Royal Horticultural Society of London (R.H.S,) (2015 edition), Descriptive terminology follows the *Plant Identification Terminology, An Illustrated Glossary,* 2$^{nd}$ edition by James G. Harris and Melinda Woolf Harris, unless where otherwise defined.

Classification:

*Family*.—Rosaceae.

*Botanical*.—*Rubus idaeus* L.

*Common name*.—Raspberry.

*Variety name*.—'DrisRaspTwentyOne'.

Parentage:

*Female parent*.—'DrisRaspTwelve' (U.S. Plant Pat. No. 30,577).

*Male parent*.—'RC448.4' (unpatented).

Plant:

*Height*.—186.20 cm.

*Width*.—153.2 cm.

*Length/width ratio*.—1.2.

*Growth habit*.—Semi-upright.

*Primocane* (*current year's cane*).—Color: RHS 135D (Light yellowish green). Cane length in autumn: 191 cm. Internodal distance at central ⅓ of cane: 5.69 cm. Anthocyanin coloration of cane: Absent or very weak. Cane bloom: Absent or very weak. Time of cane emergence: Medium.

*Very young shoot*.—Anthocyanin coloration of apex during rapid growth: Absent.

*Floricane* (*previous year's cane*).—Dormant cane color: RHS 199B (Light olive brown). Fruiting lateral attitude: Semi-erect. Fruiting lateral length: Medium.

*Prickles* (*spines*).—Presence: Present. Density: Sparse. Length at 1 m height at end of harvest (from base to tip): 0.90 mm. Color: RHS 187A (Dark red).

Leaves:

*Predominant number of leaflets*.—Three.

*Profile of leaflets in cross section*.—Straight.

*Leaf rugosity*.—Weak.

*Color of upper side*.—RHS 136A (Dark green).

*Color of lower side*.—RHS 136C (Moderate yellowish green).

*Surface texture of upper side*.—Smooth.

*Surface texture of lower side*.—Smooth.

*Terminal leaflet*.—Length: 101.9 mm. Width: 74.4 mm. Length/width ratio: 1.4. Margin: Serrate. Overall shape: Ovate. Apex shape: Cuspidate. Base shape: Cordate.

*Lateral leaflets*.—Length: 93.0 mm. Width: 55.3 mm. Length/width ratio: 1.7. Relative position of lateral leaflets: Free. Margin: Serrate. Overall shape: Ovate. Apex shape: Cuspidate. Base shape: Cordate.

*Rachis length between terminal leaflet and adjacent lateral leaflets*.—26.9 mm.

*Petiole*.—Length: 57.8 mm. Diameter: 2.72 mm. Color: RHS 136C (Moderate yellowish green).

Flowers:

*Diameter*.—30.23 mm.

*Petal*.—Length: 8.70 mm. Width: 4.07 mm. Length/width ratio: 2.1. Color of upper side: NN155C (White). Color of lower side: NN155C (White).

*Sepal*.—Length: 8.49 mm. Width: 4.36 mm. Shape: Deltoid. Color: RHS 135D (Light yellowish green).

*Pedicel*.—Length: 49.20 mm. Diameter: 1.34 mm. Color: RHS 136C (Moderate yellowish green). Surface texture: Semi-prickly.

*Peduncle*.—Color: RHS 136C (Moderate yellowish green). Anthocyanin coloration: Absent. Surface texture: Smooth with sparse prickles.

Fruit:

*Length*.—32.50 mm.

*Diameter*.—23.50 mm.

*Length/width ratio*.—1.4.

*General shape in lateral view*.—Trapezoidal.

*Color*.—RHS 42B (Strong reddish orange).

*Glossiness*.—Medium.

*Firmness*.—Firm.

*Adherence to plug*.—Weak.

*Size of single drupe*.—Large.

*Number of drupelets per berry*.—80-100.

*Average weight per berry*.—6.4 g.

*Soluble solids* (° Brix).—10.8.

Seed:

*Length*.—3 mm.

*Width*.—1 mm.

*Shape*.—Lens.

*Color*.—RHS 165B (Brownish orange).

Production:

*Main bearing type*.—Both on floricane (previous year's cane) in summer and on primocane (current year's cane) in autumn.

*Primocane* (*current year's cane*).—Time of beginning of flowering: Mid-May. Time of beginning of fruit ripening: Mid-June. Length of fruiting period: Mid-June to early November. Yield: 19,122 kg to 26,579 kg of fruit per hectare per season from 7-month-old plants when grown in Watsonville, Calif.

*Floricane* (*previous year's cane*).—Time of vegetative bud burst: Late March. Time of beginning of flowering: Mid-April. Time of beginning of fruit ripening: Mid-May. Length of fruiting period: Mid-May to late July. Yield: 31,093 kg to 48,092 kg of fruit per hectare per season from 12-month-old plants when grown in Watsonville, Calif.

Fruit storage life and shipping quality: Following harvest, fruit can be stored for 10 days if maintained under cooled temperatures that are standard for raspberry storage.

Market use: Fresh fruit.

Hardiness zone (heat/cold tolerance): Zones 4-8, preferring cool climates.

Resistance to diseases:

*Powdery mildew* (*Podosphaera macularis*).—Susceptible.

COMPARISONS TO PARENTAL AND REFERENCE RASPBERRY VARIETIES

'DrisRaspTwentyOne' differs from the female parent 'DrisRaspTwelve' (U.S. Plant Pat. No. 30,577) in that 'DrisRaspIwentyOne' has an improved shelf life and bigger fruit size when compared to 'DrisRaspTwelve'. Further, for 'DrisRaspTwentyOne' the leaves have predominantly three leaflets, the profile of leaflets in cross section is straight, and the fruit glossiness is medium, whereas for 'DrisRaspTwelve' the leaves have equally three and five leaflets, the profile of leaflets in cross section is concave, and the fruit glossiness is strong.

'DrisRaspTwentyOne' differs from the proprietary male parent 'RC448.4' (unpatented) in that 'DrisRaspTwentyOne' has an improved shelf life when compared to 'RC448.4'.

'DrisRaspTwentyOne' differs from reference raspberry variety 'Driscoll Maravilla' (U.S. Plant Pat. No. 14,804) in that for 'DrisRaspTwentyOne' the leaves have predominantly three leaflets, the relative position of the lateral leaflets is free, the fruit's adherence to the plug is weak, and the fruit shape in lateral view is trapezoidal, whereas for 'Driscoll Maravilla' the leaves have predominantly five leaflets, the relative position of the lateral leaflets is overlapping, the fruit's adherence to the plug is medium, and the fruit shape in lateral view is broad conical (ovate).

'DrisRaspTwentyOne' differs from reference raspberry variety 'DrisRaspSeven' (U.S. Plant Pat. No. 25,045) in that for 'DrisRaspTwentyOne' the bloom on current season's cane is absent or very weak, the predominant number of leaflets on leaves is three, the leaf rugosity is weak, and the fruit firmness is firm, whereas for 'DrisRaspSeven' the bloom on current season's cane is medium, the predominant number of leaflets on leaves is five, the leaf rugosity is medium, and the fruit firmness is medium.

What is claimed is:

1. A new and distinct variety of raspberry plant designated 'DrisRaspTwentyOne' as shown and described herein.

* * * * *